(12) United States Patent
Murdock

(10) Patent No.: US 10,792,232 B2
(45) Date of Patent: Oct. 6, 2020

(54) METHODS TO DELIVER ANTIFIBRINOLYTIC DRUGS FOR ANTI-AGING RESULTS

(71) Applicant: Frank Murdock, Coppell, TX (US)

(72) Inventor: Frank Murdock, Coppell, TX (US)

(73) Assignee: MURDOCK TECHNOLOGIES, LLC, Dallas, TX (US)

( * ) Notice: Subject to any disclaimer, the term of this patent is extended or adjusted under 35 U.S.C. 154(b) by 0 days.

(21) Appl. No.: 15/785,481

(22) Filed: Oct. 17, 2017

(65) Prior Publication Data

US 2018/0104163 A1 Apr. 19, 2018

Related U.S. Application Data

(60) Provisional application No. 62/409,986, filed on Oct. 19, 2016.

(51) Int. Cl.
| | |
|---|---|
| *A61K 8/36* | (2006.01) |
| *A61Q 19/08* | (2006.01) |
| *A61K 8/02* | (2006.01) |
| *A61K 8/64* | (2006.01) |
| *A61K 8/44* | (2006.01) |

(52) U.S. Cl.
CPC .............. *A61K 8/36* (2013.01); *A61K 8/0208* (2013.01); *A61K 8/44* (2013.01); *A61K 8/445* (2013.01); *A61K 8/64* (2013.01); *A61Q 19/08* (2013.01); *A61K 2800/87* (2013.01); *A61K 2800/874* (2013.01)

(58) Field of Classification Search
None
See application file for complete search history.

(56) References Cited

U.S. PATENT DOCUMENTS

| | | | |
|---|---|---|---|
| 4,883,666 A | 11/1989 | Sabel et al. | |
| 6,153,208 A * | 11/2000 | McAtee | A61K 8/0208 424/402 |
| 7,022,125 B2 | 4/2006 | Boethius | |
| 2002/0049471 A1 | 4/2002 | Boethius | |
| 2007/0015837 A1 | 1/2007 | Kun et al. | |
| 2009/0041875 A1 * | 2/2009 | Takada | A61K 8/97 424/755 |
| 2014/0271509 A1 * | 9/2014 | Claiborne | A61K 8/97 424/62 |

FOREIGN PATENT DOCUMENTS

WO    WO-2014163896 A1 * 10/2014 ............... A61K 8/46

OTHER PUBLICATIONS

Ebrahimi, B., & Naeini, F.F., Topical tranexamic acid as a promising treatment for melasma, J.Res. Med. Sci. 19 (Aug. 2014) pp. 753-757. (Year: 2014).*
Passeron, T. & Picardo, M., Melasma, a photoaging disorder, Pigment Cell Melanoma Res., 9 (2017) pp. 451-465. (Year: 2017).*
Sawaya et al., "Antifibrinolytic Therapy for Experimentally Grown Malignant Brain Tumors", *J. Neurosurg.*, vol. 64(2), pp. 263-268 (1986)—Abstract Only.
Hiramoto et al., "The Amelioration Effect of Tranexamic Acid in Wrinkles Induced by Skin Dryness", *Biomedicine & Pharmacotherapy*, vol. 80, pp. 16-22 (2016).
Pins et al., "Plasmin Triggers Rapid Contraction and Degradation of Fibroblast-Populated Collagen Lattices", *The Journal of Investigative Dermatology*, pp. 647-653 (2000).
Hiramoto et al., "Sex Difference Regarding the Amelioration of Wrinkles Due to Skin Dryness by the Administration of Tranexamic Acid", *Biomedicine & Pharmacotherapy*, vol. 83, pp. 283-289 (2016).
Kal at al., "Response of Rat Prostate and Lung Tumors to Ionizing Radiation Combined with the Angiogenesis Inhibitor AMCA", *Strahlenther Onkol*, No. 12, pp. 798-804 (2004).
Kim, S.J., et al., "Efficacy and possible mechanisms of topical tranexamic acid in melasma", Clinical and Exeperimental Dermatology, 2016, vol. 41, pp. 480-485.
Lemperle, G., et al. "A Classification of Facial Wrinkles", Plastic and Reconstructive Surgery, 2001, pp. 1735-1750.
Perelman, R., "Melasma: an Up-to-Date Comprehensive Review", Published online 2017, 32 pages.

* cited by examiner

*Primary Examiner* — Dominic Lazaro
(74) *Attorney, Agent, or Firm* — Faegre Drinker Biddle & Reath LLP

(57) ABSTRACT

Antifibrinolytic agents are administered to a human individual to treat fine lines, wrinkles and overall skin tone of the face and body, as well as inflammation and tissue degradation effects.

19 Claims, No Drawings

METHODS TO DELIVER ANTIFIBRINOLYTIC DRUGS FOR ANTI-AGING RESULTS

CROSS-REFERENCE TO RELATED APPLICATION

This application is based upon provisional application Ser. No. 62/409,986 filed Oct. 19, 2016, all of the details of which are incorporated herein by reference thereto.

FIELD OF INVENTION

This invention relates to methods to improve fine lines, wrinkles or other bodily conditions typically associated with aging by safely and effectively delivering antifibrinolytic drugs.

BACKGROUND OF THE INVENTION

In the medical and cosmetic field a great deal of time, money and effort are spent in order to reverse or slow the signs of aging. Physical issues such as wrinkles, fine lines, crow's feet, uneven skin smoothness and firmness, as well as inflammation and tissue function loss and cellular degradation area natural phenomenon and have been the foe of individuals and clinicians alike as they seek to improve on the appearance of the skin and overall health as people age. For skin issues, individuals have utilized simple to apply topical creams and moisturizing products to help hydrate the skin in order to lessen wrinkles and temporarily improve its appearance. In addition, pharmaceutical products delivered by physicians and clinicians such as dermal fillers like Juvederm (Injectable hyaluronic acid) are used to provide a temporary (9 months to a year) correction to facial wrinkles and folds and neurotoxins such as Botox (injection) are also used to bring about similar results. Neurotoxins have also been administered by clinicians to treat more general medical conditions such as excessive sweating, overactive bladder and migraine headaches. An improved method of improving the appearance of the skin would involve a safe, simple to use and pharmacologically active solution that could be applied by the individual (no injection or dermal puncture) which would bring about a noticeable change and improvement in the appearance of wrinkles and lines when administered over the course of days/weeks/months/years. In addition an improved method of reducing the signs of aging throughout the body would involve the systemic or local delivery of a safe and effective amount of a pharmacologically active agent that would slow down or reverse some of the deleterious effects of aging. The optimal agent would provide pharmacologic activity that would be quickly metabolized but that is also eliminated by the body over the course of hours or days so any deleterious effects of the agent could be mitigated by discontinuing use.

Antifibrinolytic agents such as tranexamic acid, aminoacaproic acid, aprotinin and newer strategies such as kunitz type inhibitor polypeptide and similar polypeptide structures such as KD1 are typically administered to control excessive bleeding primarily due to their ability to inhibit plasmin activation and the resulting breakdown of blood clots. U.S. Pat. No. 7,022,125 (all of the details of which are incorporated herein by reference hereto) discloses applying an antifibrinolytic agent to a substrate to effect hemostasis of a bleeding wound. Over the years an antifibrinolytic agent (tranexamic acid) has also been shown to lighten dark patches of skin when injected directly (sometimes in combination with laser therapy) into the effected area of patients with melasma (a skin pigment condition most commonly occurring as spots in people of Asian heritage). In addition, an oral form of tranexamic acid has been tested in mice that are bred to display skin dryness. The author (Hiramoto July 2016, Biomed Pharmacotherapy) found that administration of massive levels of tranexamic acid delivered orally did have an amelioration effect on wrinkles specifically caused by skin dryness and detailed how the tranexamic acid was generating results that were different for the male mice versus female. It is important to note that the dose given, 750 mg/kg/day over 20 days would equate to just over 1,000 grams of tranexamic acid. That compared to the 20 grams over the course of 5 days that is the safe and effective dose currently given to females suffering from heavy monthly bleeding. Thus the teachings of Hiramoto would lead one away from utilizing antifibrinolytic agents for the intended purpose since it has been shown that doses in excess of 80 mg/kg/day or approximately 6 grams per day have been shown to induce seizures. Further, effects brought about by 1,000 grams of the drug could not be anticipated to be antifibrinolytic effects according to the invention.

U.S. patent application Ser. No. 14/848,923, filed Sep. 9, 2015 discloses the use of antifibrinolytic drugs in connection with cancer and with concussions. All of the details of that application are incorporated herein by reference thereto.

SUMMARY OF THE INVENTION

In accordance with this invention, fine lines, wrinkles, overall skin tone of the face and body of a female or male human, as well as inflammation and tissue degradation effects are improved by the administration of an antifibrinolytic agent(s).

In accordance with this invention an area of the skin to be treated is selected. This can be a specific area, such as the face or can be the skin in general, particularly when the antifibrinolytic agent is systemically administered. The administration is preferably done on multiple consecutive days with the dosage being less than six grams per day. This results in reducing the aging effects of the area to be treated when compared with that area before the administration of the antifibrinolytic agent.

DETAILED DESCRIPTION

The present invention is based on the realization that the aging process and its physical effects on the skin and body involve the activation of a fibrinolytic process. It its broad aspect, the invention is practiced by countering a fibrinolytic process in that area (such as plasmin activity) through the administration of an antifibrinolytic agent or agents such as tranexamic acid. In a simple embodiment, a small amount (such as 1-2 ml) of a simple 10% solution (1 g/10 ml of aqueous solution) of tranexamic acid is poured from a container and applied daily to the surface of the face. Surprisingly, the liquid is almost immediately absorbed into the skin and over the course of, for example, 14-21 days, lines and wrinkles are fewer and less pronounced and overall skin tone is improved. It is anticipated that other concentrations (such as 1-150 or more) and application regimens of tranexamic acid or other antifibrinolytic agents would be beneficial as well and would be anticipated as long as they are effective and avoid negative outcomes such as prolonged redness or other dermal or bodily reactions. The invention can be practiced by the systemic and/or direct local administration of safe and effective amounts of an antifibrinolytic agent(s) whereby the drug's activity results in an overall improvement of the cellular environment and condition (such as levels of intracellular oxygen, mitochondrial function, cellular energy production and cell wall integrity) thereby reducing damage to tissues caused by aging (the impact of free radicals, enzymes, toxic proteins or reduced collagen and/or elastin amounts as examples). The dosage of antifibrinolytic agent(s) should be less than 6 grams per day. Currently approved, safe and effective systemic doses of tranexamic acid, for example, are on the order of a maximum of 4 grams per day for 5 days delivered orally for heavy menstrual bleeding and approximately 3 grams per day (via a 10% solution) for a maximum of 8 days delivered via IV injection to limit excessive bleeding in hemophiliacs undergoing tooth extraction. Effective anti-aging doses and concentrations of antifibrinolytic agent(s) could be anticipated to deviate from these ranges and could be delivered in improved delivery strategies like gels, creams, extended release pills, nano-particles or implanted/injected drug depots or local injection as long as they are effective and do not increase the incidence of thromboembolic events or other negative situations like retinal changes or seizure activity. In addition, topical dermal solutions may be preferentially packaged in volumes that are sufficient to be used over an extended period of time such as weeks or months (greater than 10 ml for example) and/or provided in a safe, controllable and easy to use formats such as reservoirs with associated premeasured dosing chambers or pumps like those utilized for delivery of hand soaps or rollerball or porous soft tipped type applicators like those that apply and deliver deodorant. A particularly advantageous manner of administration for topical delivery is by single use pre-impregnated towelettes applied to the area of the skin to be treated.

What is claimed is:

1. A method to treat the skin aging effects of one or more of lines and wrinkles of a human individual, the method comprising selecting a target area of the skin to be treated, countering plasmin activity of the fibrinolytic process by administering an antifibrinolytic agent to the individual in a dosage of less than six grams per day, and thereby reducing one or more of the skin aging effects of the target area treated as compared with that target area prior to treatment.

2. The method according to claim 1 wherein the antifibrinolytic agent is administered on multiple consecutive days.

3. The method according to claim 2 wherein the antifibrinolytic agent is administered to the body via systemic administration to improve tissue health and function or via a technique selected from the group consisting of an oral liquid, pill, I.V. injection, and implanted depot.

4. The method according to claim 3 where the administration has a time or extended release function or format.

5. The method according to claim 1 wherein the antifibrinolytic agent is administered directly to the dermal tissue surface of the target area treated via a topical solution to improve the visible appearance of the skin.

6. The method according to claim 5 where the administration is by a device which is a reservoir that enables safe and controlled delivery of the topical solution, the device being selected from the group consisting of a pump, a squeeze bottle, a calibrated chamber and combinations thereof, and a rollerball and a porous soft tipped applicator.

7. The method according to claim 1 wherein the antifibrinolytic agent is administered directly to the target area to improve tissue health and function.

8. The method according to claim 7, wherein the direct administration is direct injection made by a device selected from the group consisting of a needle and a microcatheter.

9. The method according to claim 1 wherein the target area is the face.

10. The method according to claim 1 wherein the target area is the skin in general.

11. The method according to claim 1 wherein the dosage is no greater than four grams per day.

12. The method according to claim 2 wherein the antifibrinolytic agent is tranexamic acid.

13. The method according to claim 1 wherein the antifibrinolytic agent is pre-impregnated into a towelette which is applied against the target area.

14. The method according to claim 13 wherein the towelette is a single use towelette, and on a next consecutive day a different towelette is applied against the target area.

15. The method according to claim 9 wherein antifibrinolytic agent is administered to the face on multiple consecutive days.

16. The method according to claim 1, wherein the antifibrinolytic agent is the sole active ingredient being administered.

17. The method according to claim 1 wherein the antifibrinolytic agent is administered in an amount of 1-150 ml.

18. The method according to claim 1 wherein the antifibrinolytic agent is 1-2 ml tranexamic acid of a 10% aqueous solution.

19. The method according to claim 1, where the antifibrinolytic agent is the primary active ingredient being administered to combat lines and wrinkles.

* * * * *